United States Patent
Schultz

(10) Patent No.: US 8,380,276 B2
(45) Date of Patent: Feb. 19, 2013

(54) CATHETER WITH THIN FILM PRESSURE SENSING DISTAL TIP

(75) Inventor: Jeffrey W. Schultz, Chino, CA (US)

(73) Assignee: Biosense Webster, Inc., Diamond Bar, CA (US)

(*) Notice: Subject to any disclaimer, the term of this patent is extended or adjusted under 35 U.S.C. 154(b) by 0 days.

(21) Appl. No.: 12/857,342

(22) Filed: Aug. 16, 2010

(65) Prior Publication Data

US 2012/0041295 A1    Feb. 16, 2012

(51) Int. Cl.
*A61B 5/04* (2006.01)
*A61B 18/14* (2006.01)

(52) U.S. Cl. .......................... 600/374; 606/41

(58) Field of Classification Search ........... 600/374; 606/41
See application file for complete search history.

(56) References Cited

U.S. PATENT DOCUMENTS

| | | |
|---|---|---|
| 3,971,364 A | 7/1976 | Fletcher et al. |
| 4,764,114 A | 8/1988 | Jeffcoat et al. |
| 4,856,993 A | 8/1989 | Maness et al. |
| 5,263,493 A | 11/1993 | Avitall |
| 5,368,564 A | 11/1994 | Savage |
| 5,391,199 A | 2/1995 | Ben-Haim |
| 5,487,757 A | 1/1996 | Truckai et al. |
| 5,499,542 A | 3/1996 | Morlan |
| 5,558,091 A | 9/1996 | Acker et al. |
| 5,563,354 A | 10/1996 | Kropp |
| 5,662,124 A | 9/1997 | Wilk |
| 5,673,695 A | 10/1997 | McGee et al. |
| 5,680,860 A | 10/1997 | Imran |
| 5,685,878 A | 11/1997 | Falwell et al. |
| 5,769,843 A | 6/1998 | Abela et al. |
| 5,826,576 A | 10/1998 | West |
| 5,833,608 A | 11/1998 | Acker |
| 5,836,894 A | 11/1998 | Sarvazyan |

(Continued)

FOREIGN PATENT DOCUMENTS

| | | |
|---|---|---|
| DE | 19750441 A1 | 6/1999 |
| EP | 0 928 601 A1 | 7/1999 |

(Continued)

OTHER PUBLICATIONS

Extended European Search Report dated Nov. 17, 2011 for European patent application No. 11177600.1 (5 pages).

(Continued)

*Primary Examiner* — Lee Cohen
(74) *Attorney, Agent, or Firm* — Christie, Parker & Hale, LLP

(57) ABSTRACT

A mapping and ablation catheter has contact force sensing capabilities at a distal end. In one embodiment, the catheter includes a catheter body, a deflectable section, and a tip distal tip section which has a tip electrode with a thin-film pressure sensor that is adapted to detect a force vector applied to the tip electrode. The thin-film pressure sensor includes two opposing flexible and thin support members containing a pressure-sensitive material therebetween whose resistivity changes as a result of pressure and is detected by trace electrode intersections supported on interfacing surfaces of the flexible and thin support members. Used with a stop member having a conforming shape against which the thin-film pressure sensor abuts when a force vector is applied to the tip electrode, the pressure sensor can have a 2-D, radially-symmetrical shape, e.g., a disc or ring configuration, or a 3-D, radially-symmetrical shape, e.g., a conical configuration.

20 Claims, 15 Drawing Sheets

U.S. PATENT DOCUMENTS

| | | |
|---|---|---|
| 5,860,974 A | 1/1999 | Abele |
| 5,902,248 A | 5/1999 | Millar et al. |
| 5,916,147 A | 6/1999 | Boury |
| 5,944,022 A | 8/1999 | Nardella et al. |
| 5,947,320 A | 9/1999 | Bordner et al. |
| 5,964,757 A | 10/1999 | Ponzi |
| 5,974,320 A | 10/1999 | Ward et al. |
| 5,983,126 A | 11/1999 | Wittkampf |
| 6,048,329 A | 4/2000 | Thompson et al. |
| 6,063,022 A | 5/2000 | Ben-Haim |
| 6,123,699 A | 9/2000 | Webster, Jr. |
| 6,171,277 B1 | 1/2001 | Ponzi |
| 6,177,792 B1 | 1/2001 | Govari et al. |
| 6,183,463 B1 | 2/2001 | Webster, Jr. |
| 6,198,974 B1 | 3/2001 | Webster, Jr. |
| 6,201,387 B1 | 3/2001 | Govari |
| 6,203,493 B1 | 3/2001 | Ben-Haim |
| 6,216,027 B1 | 4/2001 | Willis et al. |
| 6,226,542 B1 | 5/2001 | Reisfeld |
| 6,239,724 B1 | 5/2001 | Doron et al. |
| 6,241,724 B1 | 6/2001 | Fleischman et al. |
| 6,272,371 B1 | 8/2001 | Shlomo |
| 6,272,672 B1 | 8/2001 | Conway |
| 6,301,496 B1 | 10/2001 | Reisfeld |
| 6,332,089 B1 | 12/2001 | Acker et al. |
| 6,335,617 B1 | 1/2002 | Osadchy et al. |
| 6,436,059 B1 | 8/2002 | Zanelli |
| 6,456,864 B1 | 9/2002 | Swanson et al. |
| 6,484,118 B1 | 11/2002 | Govari |
| 6,551,302 B1 | 4/2003 | Rosinko et al. |
| 6,574,492 B1 | 6/2003 | Ben-Haim et al. |
| 6,584,856 B1 | 7/2003 | Biter et al. |
| 6,602,242 B1 | 8/2003 | Fung et al. |
| 6,612,992 B1 | 9/2003 | Hossack et al. |
| 6,618,612 B1 | 9/2003 | Acker et al. |
| 6,690,963 B2 | 2/2004 | Ben-Haim et al. |
| 6,695,808 B2 | 2/2004 | Tom |
| 6,711,429 B1 | 3/2004 | Gilboa et al. |
| 6,727,371 B2 | 4/2004 | Müller et al. |
| 6,814,733 B2 | 11/2004 | Leatham et al. |
| 6,892,091 B1 | 5/2005 | Ben-Haim et al. |
| 6,915,149 B2 | 7/2005 | Ben-Haim |
| 6,945,956 B2 | 9/2005 | Waldhauser et al. |
| 6,964,205 B2 | 11/2005 | Papakostas et al. |
| 6,973,339 B2 | 12/2005 | Govari |
| 6,997,924 B2 | 2/2006 | Schwartz et al. |
| 7,077,823 B2 | 7/2006 | McDaniel |
| 7,156,816 B2 | 1/2007 | Schwartz et al. |
| 7,235,070 B2 | 6/2007 | Vanney |
| 7,306,593 B2 | 12/2007 | Keidar et al. |
| 7,311,704 B2 | 12/2007 | Paul et al. |
| 7,397,364 B2 | 7/2008 | Govari |
| 7,481,774 B2 | 1/2009 | Brockway et al. |
| 7,536,218 B2 | 5/2009 | Govari et al. |
| 7,604,605 B2 | 10/2009 | Zvuloni |
| 7,681,432 B2 | 3/2010 | Hay et al. |
| 7,686,767 B2 | 3/2010 | Maschke |
| 8,083,691 B2 | 12/2011 | Goldenberg et al. |
| 2001/0047129 A1 | 11/2001 | Hall et al. |
| 2001/0047133 A1 | 11/2001 | Gilboa et al. |
| 2002/0002329 A1 | 1/2002 | Avitall |
| 2002/0065455 A1 | 5/2002 | Ben-Haim et al. |
| 2002/0068866 A1 | 6/2002 | Zikorus et al. |
| 2002/0165461 A1 | 11/2002 | Hayzelden et al. |
| 2002/0193781 A1 | 12/2002 | Loeb |
| 2003/0120150 A1 | 6/2003 | Govari |
| 2003/0120195 A1 | 6/2003 | Milo et al. |
| 2003/0130615 A1 | 7/2003 | Tom |
| 2003/0158494 A1 | 8/2003 | Dahl et al. |
| 2004/0049255 A1 | 3/2004 | Jain et al. |
| 2004/0064024 A1 | 4/2004 | Sommer |
| 2004/0068178 A1 | 4/2004 | Govari |
| 2004/0097806 A1 | 5/2004 | Hunter et al. |
| 2004/0102769 A1 | 5/2004 | Schwartz et al. |
| 2004/0147920 A1 | 7/2004 | Keidar |
| 2004/0244464 A1 | 12/2004 | Hajdukiewicz et al. |
| 2004/0254458 A1 | 12/2004 | Govari |
| 2005/0033135 A1 | 2/2005 | Govari |
| 2005/0080429 A1 | 4/2005 | Freyman et al. |
| 2005/0277875 A1 | 12/2005 | Selkee |
| 2006/0009690 A1 | 1/2006 | Fuimaono et al. |
| 2006/0009735 A1 | 1/2006 | Viswanathan et al. |
| 2006/0015096 A1 | 1/2006 | Hauck et al. |
| 2006/0173480 A1 | 8/2006 | Zhang |
| 2006/0200049 A1 | 9/2006 | Leo et al. |
| 2006/0247618 A1 | 11/2006 | Kaplan et al. |
| 2007/0021742 A1 | 1/2007 | Viswanathan |
| 2007/0060832 A1 | 3/2007 | Levin |
| 2007/0060847 A1 | 3/2007 | Leo et al. |
| 2007/0106114 A1 | 5/2007 | Sugimoto et al. |
| 2007/0142749 A1 | 6/2007 | Khatib et al. |
| 2007/0151391 A1 | 7/2007 | Larkin et al. |
| 2007/0156114 A1 | 7/2007 | Worley et al. |
| 2007/0179492 A1 | 8/2007 | Pappone |
| 2007/0185397 A1 | 8/2007 | Govari et al. |
| 2007/0191829 A1 | 8/2007 | McGee et al. |
| 2007/0197939 A1 | 8/2007 | Wallace et al. |
| 2007/0282211 A1 | 12/2007 | Ofek et al. |
| 2008/0009750 A1 | 1/2008 | Aeby et al. |
| 2008/0015568 A1 | 1/2008 | Paul et al. |
| 2008/0051704 A1 | 2/2008 | Patel et al. |
| 2008/0065111 A1 | 3/2008 | Blumenkranz et al. |
| 2008/0071267 A1 | 3/2008 | Wang et al. |
| 2008/0077049 A1 | 3/2008 | Hirshman |
| 2008/0183075 A1 | 7/2008 | Govari et al. |
| 2008/0249522 A1 | 10/2008 | Pappone et al. |
| 2008/0255540 A1 | 10/2008 | Selkee |
| 2008/0275428 A1 | 11/2008 | Tegg et al. |
| 2008/0275442 A1* | 11/2008 | Paul et al. ................ 606/41 |
| 2008/0275465 A1 | 11/2008 | Paul et al. |
| 2008/0281319 A1 | 11/2008 | Paul et al. |
| 2008/0287777 A1 | 11/2008 | Li et al. |
| 2008/0288038 A1 | 11/2008 | Paul et al. |
| 2008/0294144 A1 | 11/2008 | Leo et al. |
| 2008/0294158 A1 | 11/2008 | Pappone et al. |
| 2009/0010021 A1 | 1/2009 | Smith et al. |
| 2009/0093806 A1 | 4/2009 | Govari et al. |
| 2009/0138007 A1 | 5/2009 | Govari et al. |
| 2009/0158511 A1 | 6/2009 | Maze et al. |
| 2009/0287118 A1 | 11/2009 | Malek |
| 2009/0306650 A1 | 12/2009 | Govari et al. |
| 2010/0063478 A1 | 3/2010 | Selkee |
| 2010/0137845 A1 | 6/2010 | Ramstein et al. |
| 2010/0152574 A1 | 6/2010 | Erdman et al. |
| 2010/0168620 A1 | 7/2010 | Klimovitch et al. |
| 2010/0168918 A1 | 7/2010 | Zhao et al. |
| 2011/0130648 A1 | 6/2011 | Beeckler et al. |
| 2011/0184406 A1* | 7/2011 | Selkee ..................... 606/41 |

FOREIGN PATENT DOCUMENTS

| | | |
|---|---|---|
| EP | 1 502 555 | 2/2005 |
| EP | 1 586 281 A1 | 10/2005 |
| EP | 1 690 564 | 8/2006 |
| EP | 1 743 575 A2 | 1/2007 |
| EP | 1 820 464 A1 | 8/2007 |
| EP | 1 897 581 A2 | 3/2008 |
| EP | 2 000 789 A2 | 12/2008 |
| EP | 2 047 797 A2 | 4/2009 |
| EP | 2 127 604 A1 | 12/2009 |
| EP | 2 130 508 A2 | 12/2009 |
| EP | 2 172 240 A1 | 4/2010 |
| EP | 2 338 411 A1 | 6/2011 |
| EP | 2 338 412 A1 | 6/2011 |
| JP | 2005-345215 A | 12/2005 |
| JP | 2006064465 A | 9/2006 |
| WO | WO 95/10326 | 4/1995 |
| WO | WO 96/05768 | 2/1996 |
| WO | WO 97/29678 | 8/1997 |
| WO | WO 97/29709 | 8/1997 |
| WO | WO 97/29710 | 8/1997 |
| WO | WO 98/29032 | 7/1998 |
| WO | WO 03/020139 A2 | 3/2003 |
| WO | WO 2006/086152 A2 | 8/2006 |
| WO | WO 2006/092563 A1 | 9/2006 |

| WO | WO 2007/025230 A2 | 3/2007 |
| WO | WO 2007/050960 A2 | 5/2007 |
| WO | WO 2007/067938 | 6/2007 |
| WO | WO 2007/082216 A1 | 7/2007 |
| WO | WO 2007/098494 A1 | 8/2007 |
| WO | WO 2007/111182 A1 | 10/2007 |
| WO | WO 2009/085470 A1 | 7/2009 |
| WO | WO 2009/147399 A1 | 12/2009 |
| WO | WO 2010/008975 A2 | 1/2010 |

OTHER PUBLICATIONS

Okumura, Yasuo, M.D., et al., "A Systematic Analysis of In Vivo Contact Forces on Virtual Catheter Tip/Tissue Surface Contact during Cardiac Mapping and Intervention", Journal of Cardiovascular Electrophysiology, vol. 19, No. 6, Jun. 2008, pp. 632-640.

* cited by examiner

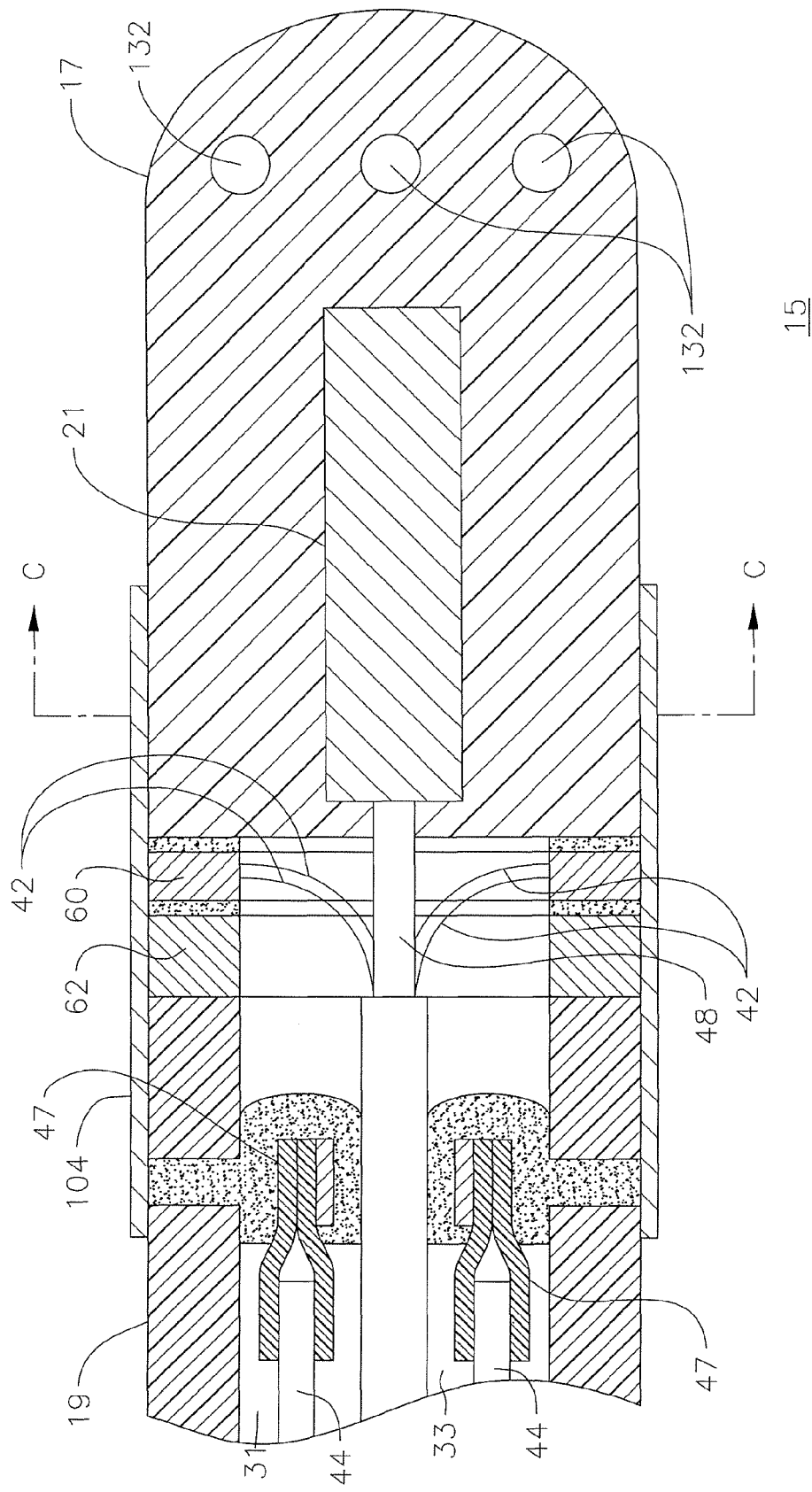

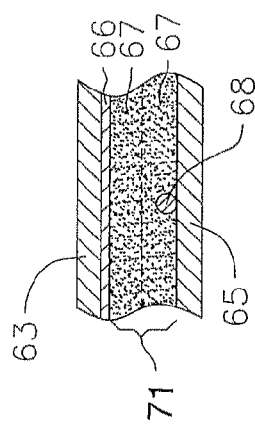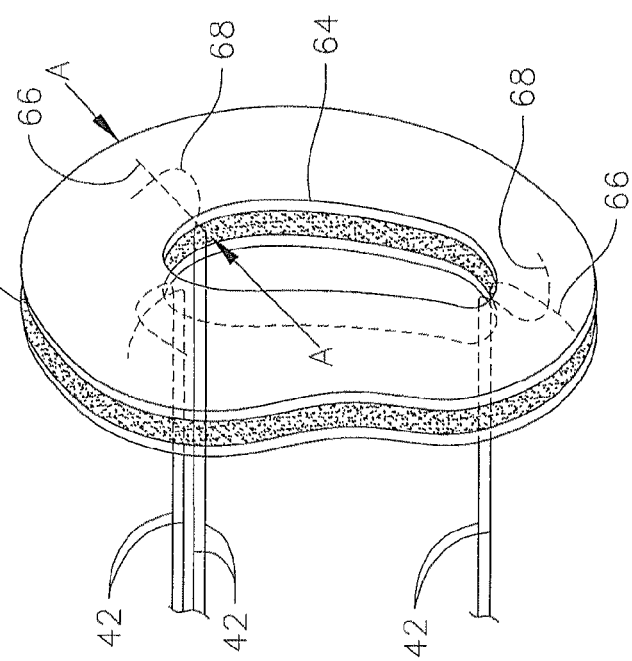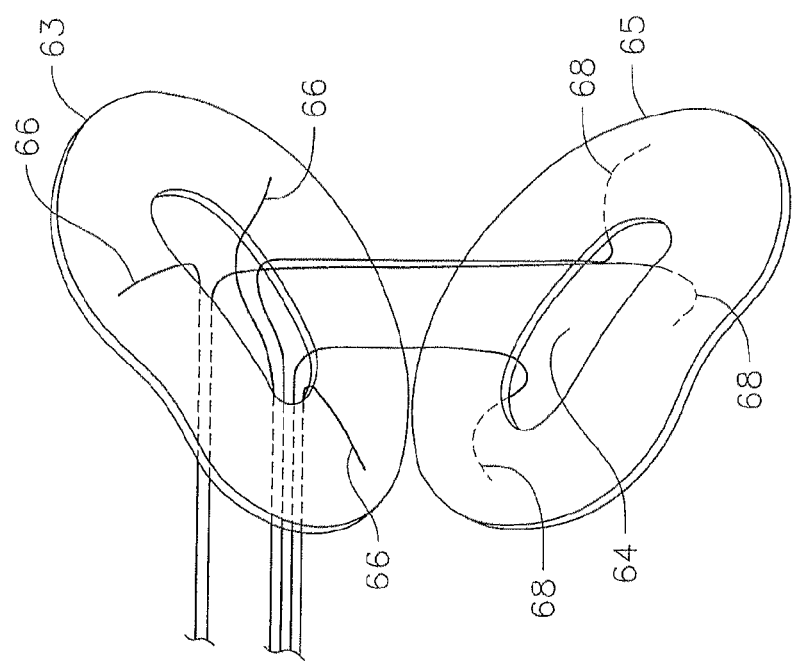

CATHETER WITH THIN FILM PRESSURE SENSING DISTAL TIP

FIELD OF INVENTION

The present invention relates to an electrophysiologic catheter useful for ablation and sensing electrical activity of heart tissue, in particular, an electrophysiologic catheter with contact force sensing capabilities at its distal end.

BACKGROUND OF INVENTION

Cardiac arrythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self propagating. Alternatively, or in addition to the multiwavelet reentrant type, cardiac arrhythmias may also have a focal origin, such as when an isolated region of tissue in an atrium fires autonomously in a rapid, repetitive fashion.

Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

Diagnosis and treatment of cardiac arrythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure—mapping followed by ablation—electrical activity at points within the heart is typically sensed and measured by advancing a catheter containing one or more electrical sensors (or electrodes) into the heart, and acquiring data at a multiplicity of points. These data are then utilized to select the endocardial target areas at which ablation is to be performed.

Ablation and mapping involves contacting tissue wall with the tip electrode of the catheter. However, proper positioning of the tip electrode relative to tissue wall is not always possible. It is therefore desirable to provide catheters with contact force sensing at a distal tip. Recent studies have suggested that lesion depth may be dependent on contact force of the tip electrode against tissue wall during RF ablation.

Accordingly, it is desirable that a catheter be adapted for mapping and ablation with contact force sensing at the distal tip electrode. It is also desirable that such a catheter be equipped with a thin-film pressure sensor for detecting, measuring and/or determining a three dimensional contact force vector acting upon the catheter tip. Since the catheter location is monitored using a magnetic-based location sensor and the heart chamber walls are mapped in 3D, it is possible to determine the tip electrode contact area in relation to the heart wall and thus calculate the tip electrode contact pressure.

SUMMARY OF THE INVENTION

The present invention is directed to a mapping and ablation catheter with contact force sensing capabilities at a distal end. In one embodiment, the catheter includes a catheter body, a deflectable section, and a tip distal tip section which has a tip electrode with a thin-film pressure sensor that is adapted to detect a force vector applied to the tip electrode. The thin-film pressure sensor includes two opposing flexible and thin support members containing a pressure-sensitive material therebetween whose resistivity is responsive to and changes as a result of pressure. The thin-film pressure further includes trace electrode intersections supported on interfacing surfaces of the flexible and thin support members to detect the change in resistivity of the pressure sensitive material between the intersections and provide signals by which a signal processor can determine radial and axial components of the force vector.

In one embodiment, the thin-film pressure sensor is has 2-D, radially-symmetrical shape, e.g., a disc or ring configuration, and is positioned on axis with the longitudinal axis of the distal tip section of the catheter. In a planar position perpendicular to the longitudinal axis, the thin-film pressure sensor is sandwiched between the tip electrode and a stop member against which the pressure sensor abuts to detect a contact force applied to the tip electrode such as when the tip electrode comes in contact with tissue wall.

In another embodiment, the thin-film pressure sensor has a 3-D, radially-symmetrical shape that allows it to rest between a conforming 3-D distal end of the stop member and a conforming 3-D proximal end of the tip electrode. The 3-D configuration enables greater sensitivity in the pressure sensor to detect radial and axial components of the contact force vector acting on the tip electrode. For example, the 3-D thin-film pressure sensor has a conical shape that conforms to a concave conical distal end of a stop member and a convex conical proximal end of a tip electrode such that the pressure sensor is nested therebetween. The proximal end of the tip electrode and the distal end of the stop member may be rotatably and pivotably coupled through a hole in the pressure sensor such as by a ball and socket coupling that allows relative movement between the tip electrode and the stop member in the radial and axial directions.

BRIEF DESCRIPTION OF THE DRAWINGS

These and other features and advantages of the present invention will be better understood by reference to the following detailed description when considered in conjunction with the accompanying drawings wherein:

FIG. 4B is a side cross-sectional view of the distal tip section of FIG. 3, as assembled, taken generally along a second diameter.

FIG. 5 is an exploded view of an embodiment of a 2-D pressure sensor, without the pressure-sensitive material.

FIG. 6 is an isometric view of the 2-D pressure sensor of FIG. 5, as assembled.

FIG. 6A is a cross-sectional view of the 2-D pressure of FIG. 6, taken along line A-A.

DETAILED DESCRIPTION OF THE INVENTION

Figure 1:
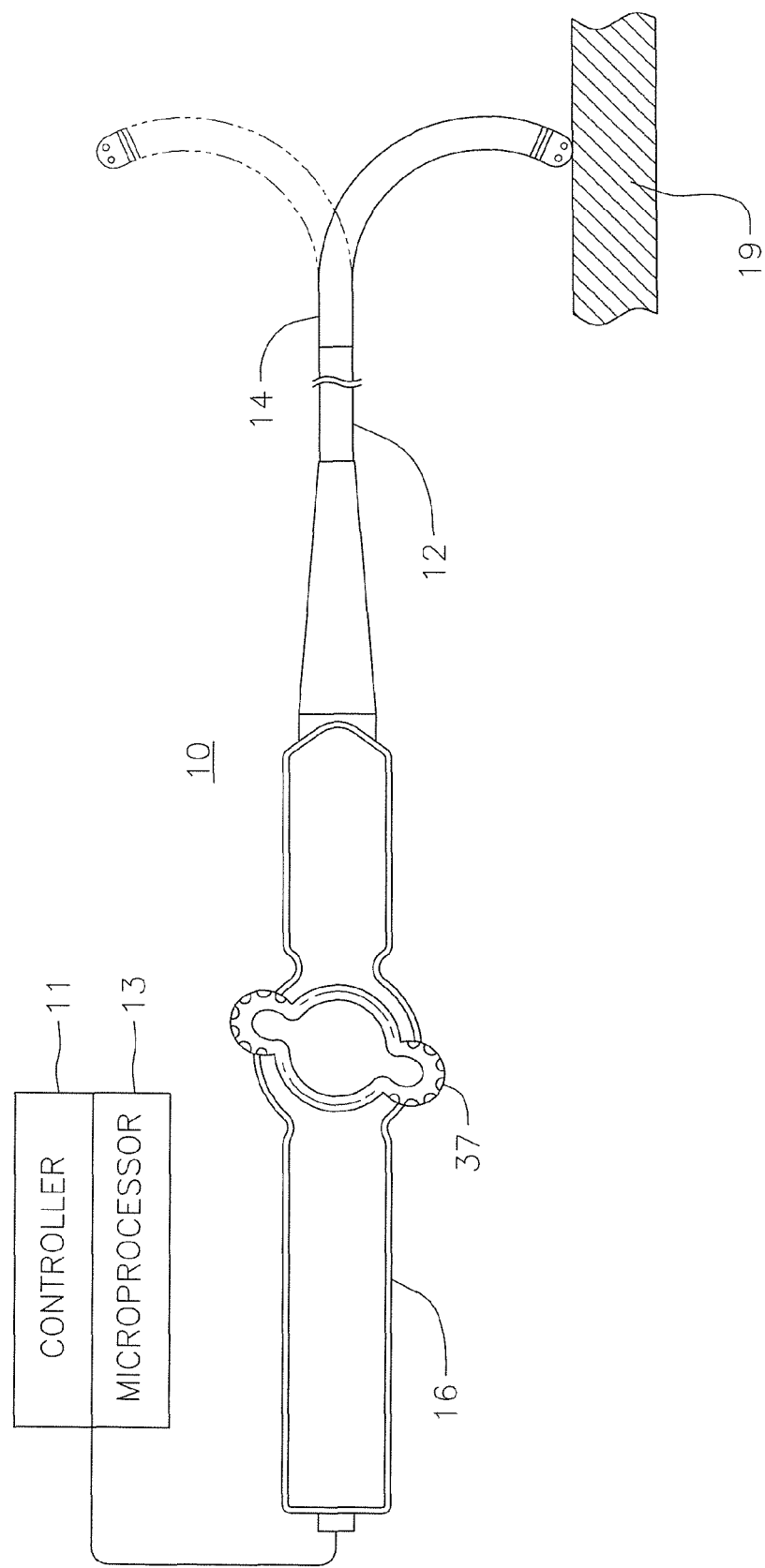
FIG. 1 is a top plan view of an embodiment of the catheter of the present invention.

FIG. 1 illustrates an embodiment of a catheter 10 with force-sensing capabilities at a distal tip. The catheter has an elongated catheter body 12 with proximal and distal ends, an intermediate deflectable section 14 at the distal end of the catheter body 12, and a distal tip section 15 adapted for mapping, ablation and detecting forces applied to a tip electrode 17 such as when the tip electrode is in contact with tissue wall 19. The catheter also includes a control handle 16 at the proximal end of the catheter body 12 where the control handle is adapted for controlling bi-directional deflection of the intermediate section 14. The control handle 16 may further serve as a conduit to a controller 11 adapted to send, receive and process electrical input and output signals to and from the distal tip section 15 for mapping, ablation and/or force-sensing, such as by means of a microprocessor 13 applying program algorithms with force-sensing solutions. In accordance with the present invention, such signals include signals from a thin-film pressure sensor with trace electrode intersections for directly measuring contact force, including detecting and measuring radial and/or axial contact forces on the tip electrode, whereby the controller and microprocessor are adapted to processes such signals in computing a contact force vector. Amplifiers and data acquisition (DAQ) equipment may be provided within the control handle to convert measurements from the thin film pressure sensor into usable signals. These equipment may also be provided externally to the catheter such as in a separate junction box or in a catheter navigation system designed to visualise real-time calculated position and orientation of a catheter within the patient's heart, such as the CARTO navigation system manufactured by Biosense Webster, Inc.

Figure 2A:
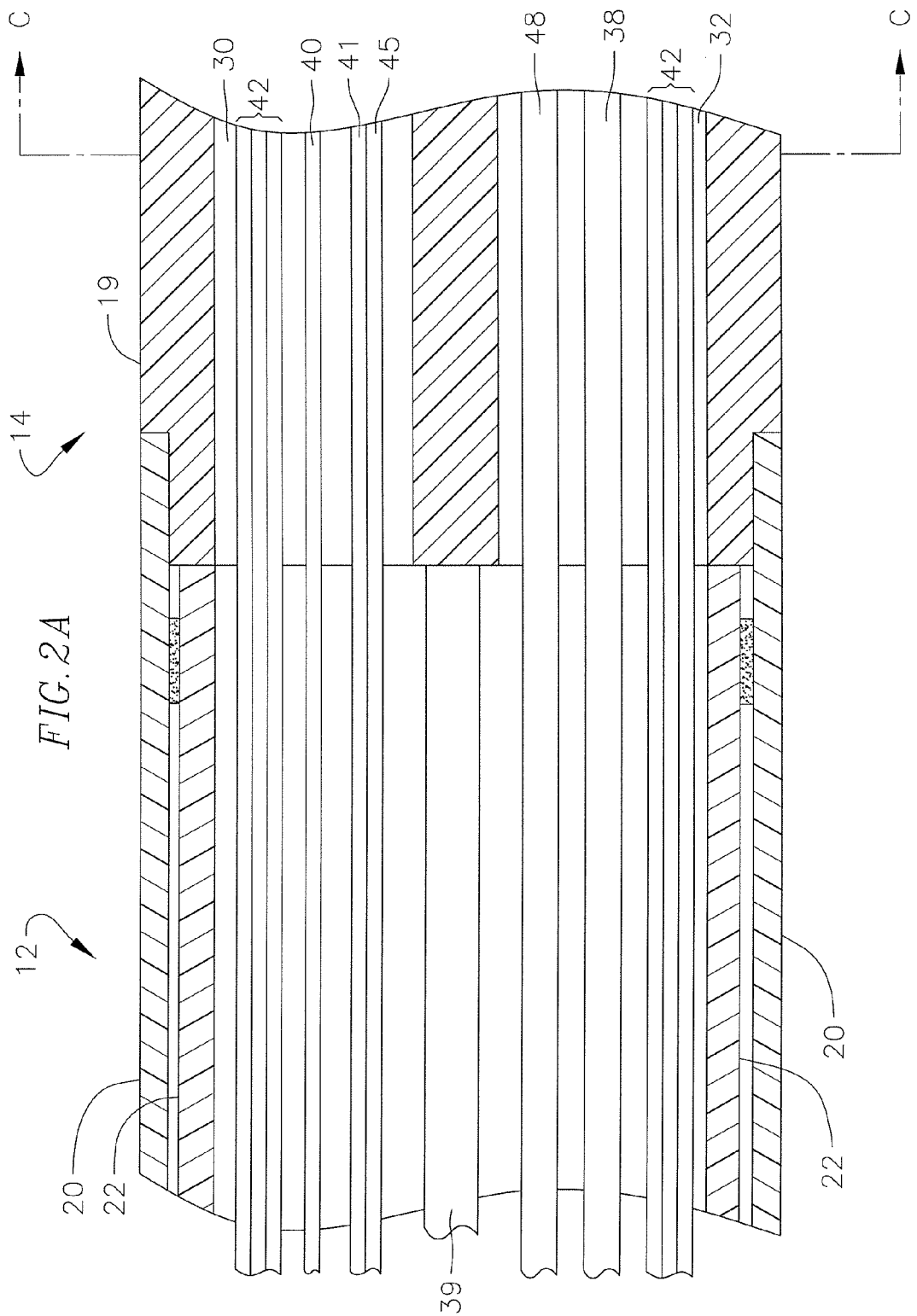
FIG. 2A is a side cross-sectional view of the catheter of FIG. 1, including a junction of the catheter body and an intermediate section taken along a first diameter.
Figure 2B:
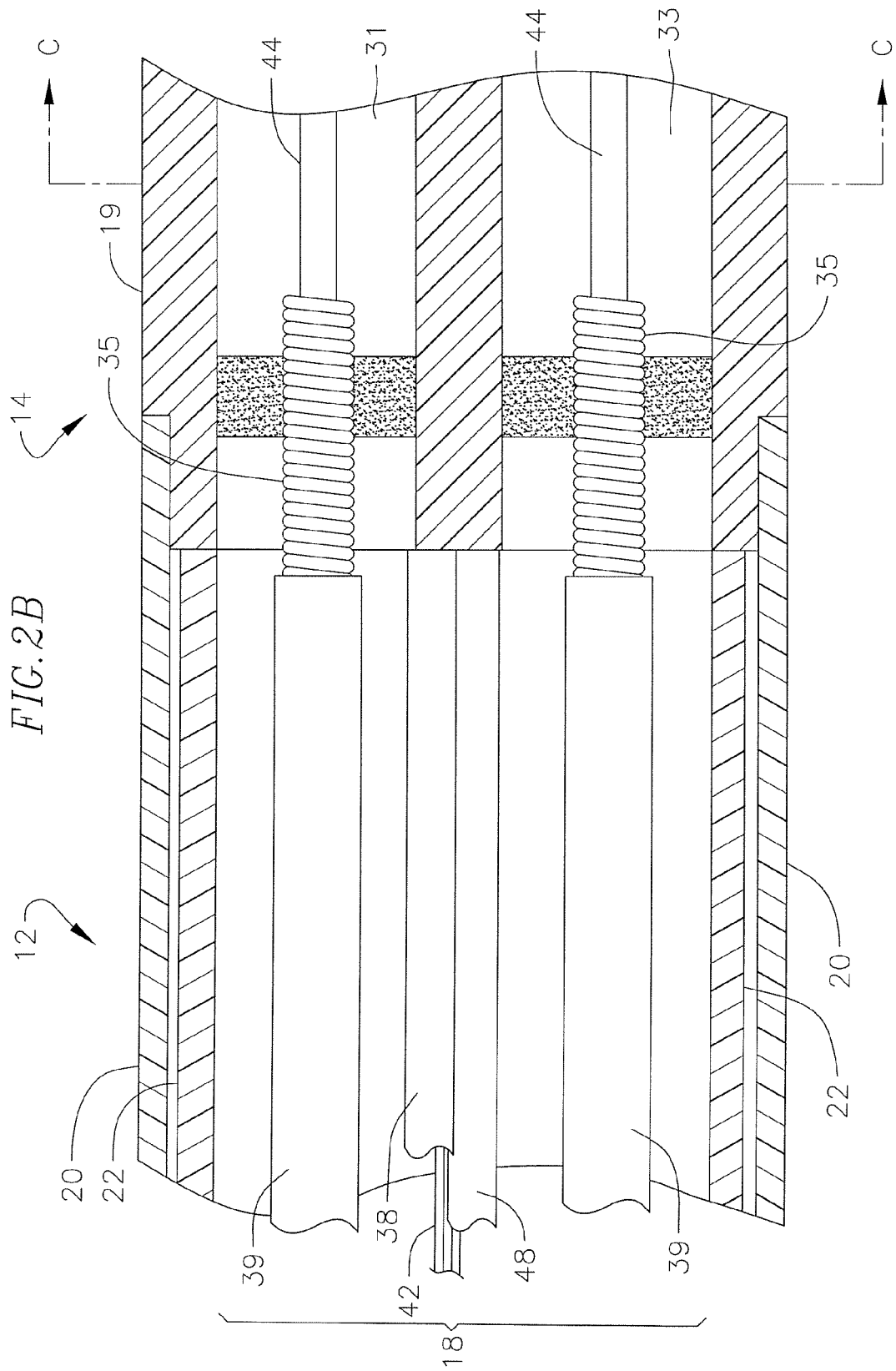
FIG. 2B is a side cross-sectional view of the catheter of FIG. 1, including a junction of the catheter body and an intermediate section taken along a second diameter generally perpendicular to the first diameter.

With reference to FIGS. 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate wires, cables, tubings and the like. If desired, the inner surface of the outer wall 20 is lined with a stiffening tube 22 to provide improved torsional stability. In a disclosed embodiment, the catheter has an outer wall 20 with an outer diameter of from about 0.090 inch to about 0.100 inch and an inner diameter of from about 0.061 inch to about 0.065 inch. Distal ends of the stiffening tube 22 and the outer wall 20 are fixedly attached to each other by adhesive bonds therebetween near the distal end and proximal ends of the catheter body 12.

Components that extend between the control handle 16 and the deflectable section 14 pass through the central lumen 18 of the catheter body 12. These components include lead wire 40 for the tip electrode 17, lead wires 42 for the pressure sensor in the tip section, an irrigation tubing 38 for delivering fluids to the tip electrode 17, a cable 48 for an electromagnetic position location sensor 21 housed in the tip electrode 17, thermocouple wires 41, 43 for sensing temperature of the tip electrode, and a pair of puller wires 44 for bidirectional deflection of the intermediate section 14.

Figure 2C:
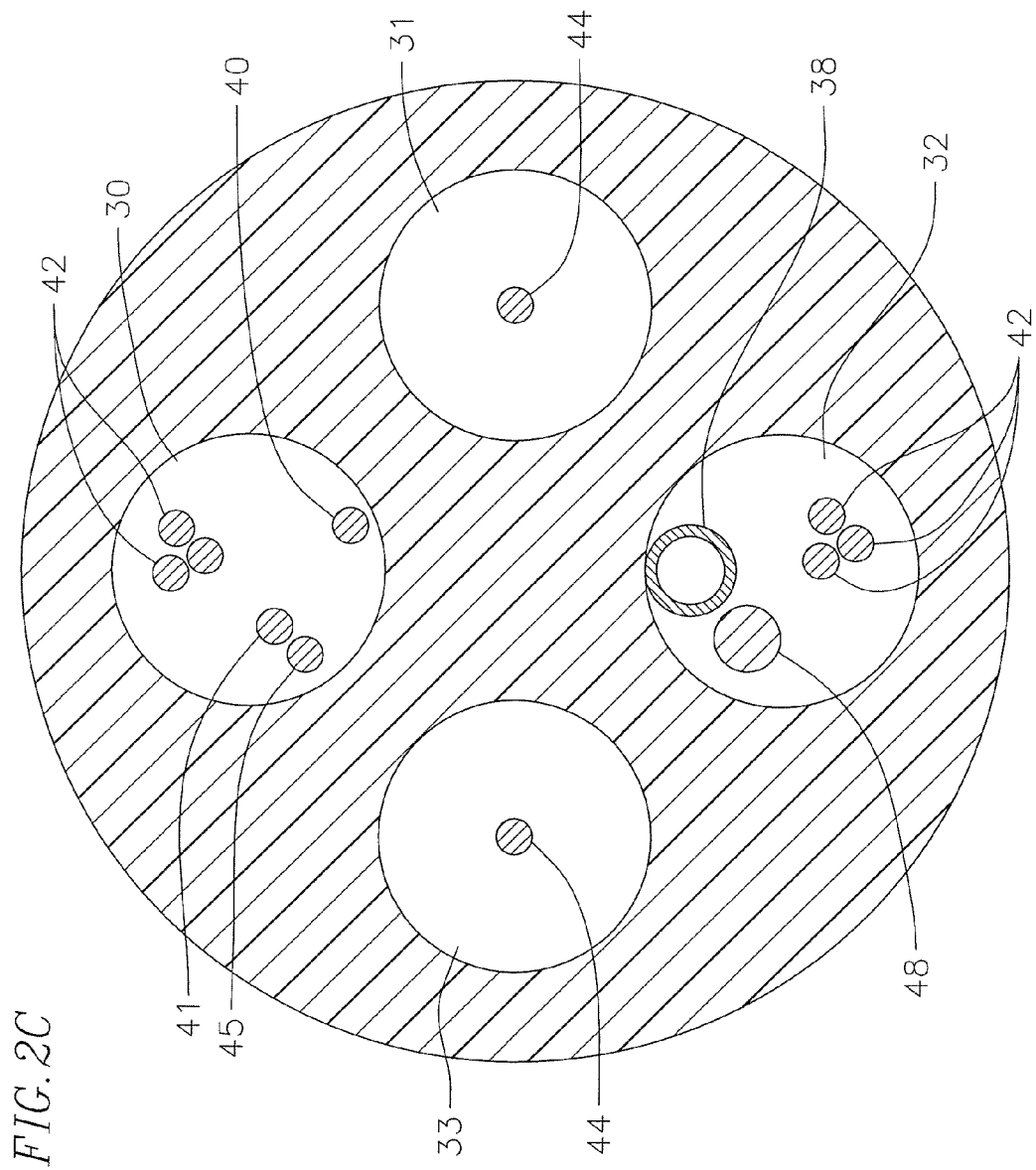
FIG. 2C is an end cross-sectional view of the embodiment of FIGS. 2A and 2C, taken alone line C-C.

Also illustrated in FIGS. 2A, 2B and 2C is an embodiment of the deflectable intermediate section 14 which comprises a shorter section of tubing 19. The tubing also has a braided mesh construction but with multiple off-axis lumens, for example first, second, third and fourth lumens 30, 31, 32 and 33. In the illustrated embodiment, each of diametrically opposing second and fourth lumens 31 and 33 carries one puller wire 44 for bi-directional deflection. The first lumen 30 carries the lead wires 40 and 42, and the thermocouple wires 41, 43. The third lumen 32 carries the irrigation tubing 38 and the sensor cable 48 and additional lead wires 42.

The tubing 19 of the intermediate section 14 is made of a suitable non-toxic material that is more flexible than the catheter body 12. A suitable material for the tubing 19 is braided polyurethane, i.e., polyurethane or PEBAX with an embedded mesh of braided stainless steel or the like. The size of each lumen is not critical so long it each lumen is sufficiently sized to house the respective components extending therethrough.

A means for attaching the catheter body 12 to the tubing 19 of the intermediate section 14 is illustrated in FIGS. 2A and 2B. The proximal end of the intermediate section 14 comprises an outer circumferential notch that receives an inner surface of the outer wall 20 of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

Each puller wire 44 is preferably coated with Teflon®. The puller wires 44 can be made of any suitable metal, such as stainless steel or Nitinol and the Teflon coating imparts lubricity to the puller wire. The puller wire preferably has a diameter ranging from about 0.006 to about 0.010 inch. As shown in FIGS. 2B and 2C, a portion of each puller wire 44 in the catheter body 12 passes through a compression coil 35 in surrounding relation to its puller wire 44. The compression coil 35 extends from the proximal end of the catheter body 12 to the proximal end of the intermediate section 14. The compression coil 35 is made of any suitable metal, preferably stainless steel, and is tightly wound on itself to provide flexibility, i.e., bending, but to resist compression. The inner diameter of the compression coil is slightly larger than the diameter of the puller wire 44. Within the catheter body 12, the outer surface of the compression coil 35 is also covered by a flexible, non-conductive sheath 39, e.g., made of polyimide tubing.

Proximal ends of the puller wires 44 are anchored in the control handle 16. Distal ends of the puller wires are anchored near the distal end of the intermediate section 14 as shown in FIG. 4B. The distal end of each puller wire is provided with a T-shaped anchor 47 that includes a short piece of tubular stainless steel, e.g., hypodermic stock, that is fitted over and crimped onto the distal end of the puller wire. The tubular stainless steel is fixed, e.g., by welding, to a cross-piece formed of stainless steel ribbon or the like. The cross-piece is fixedly secured to the outer wall of the tubing 19 to anchor the distal end of each puller wire. A first puller wire passes through the second lumen 31 and a second puller wire passes through the fourth lumen 33 of the deflectable intermediate section 14. Separate and independent longitudinal movement of the deflection wires 44 relative to the catheter body 12, which results in deflection of the intermediate section 14 and hence steering of the tip section 15 is accomplished by suitable manipulation of a deflection member 37 (FIG. 1).

Figure 3:
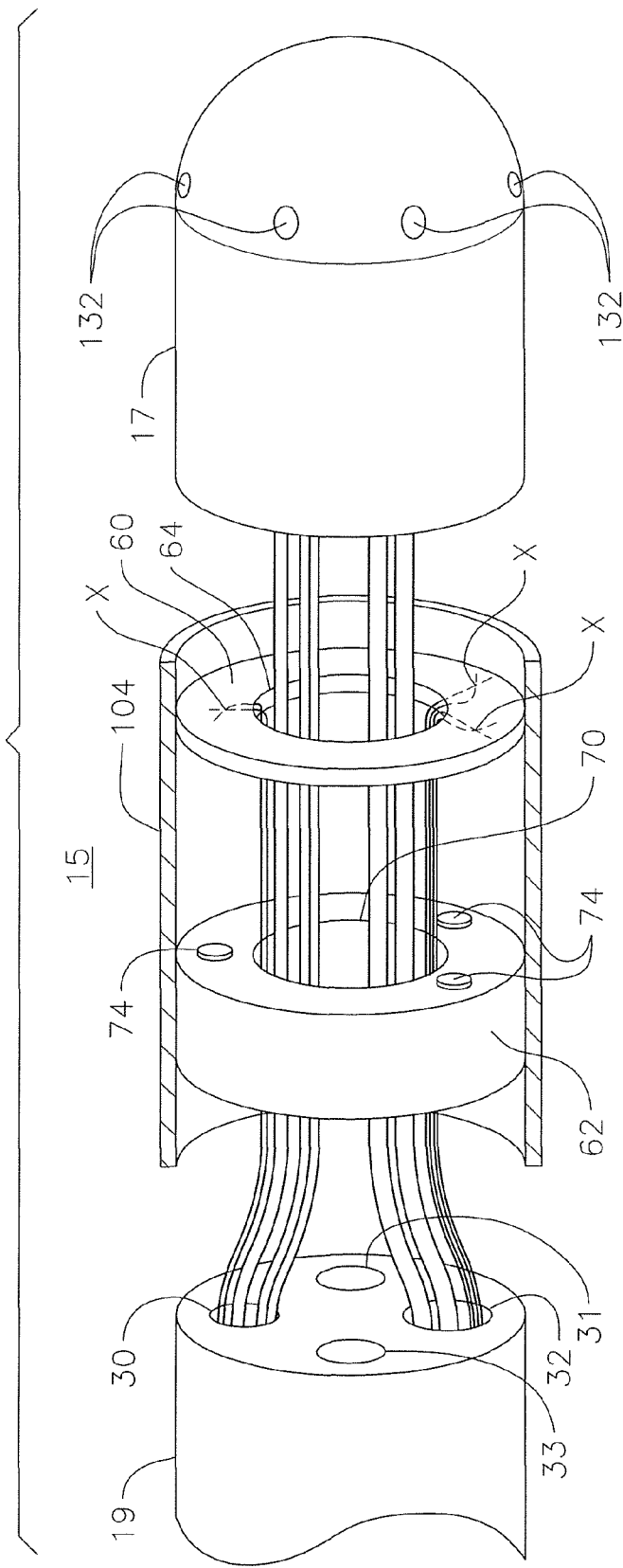
FIG. 3 is an exploded view of an embodiment of a distal tip section of the catheter of the present invention, including a tip electrode and a 2-D thin-film pressure sensor.
Figure 4A:
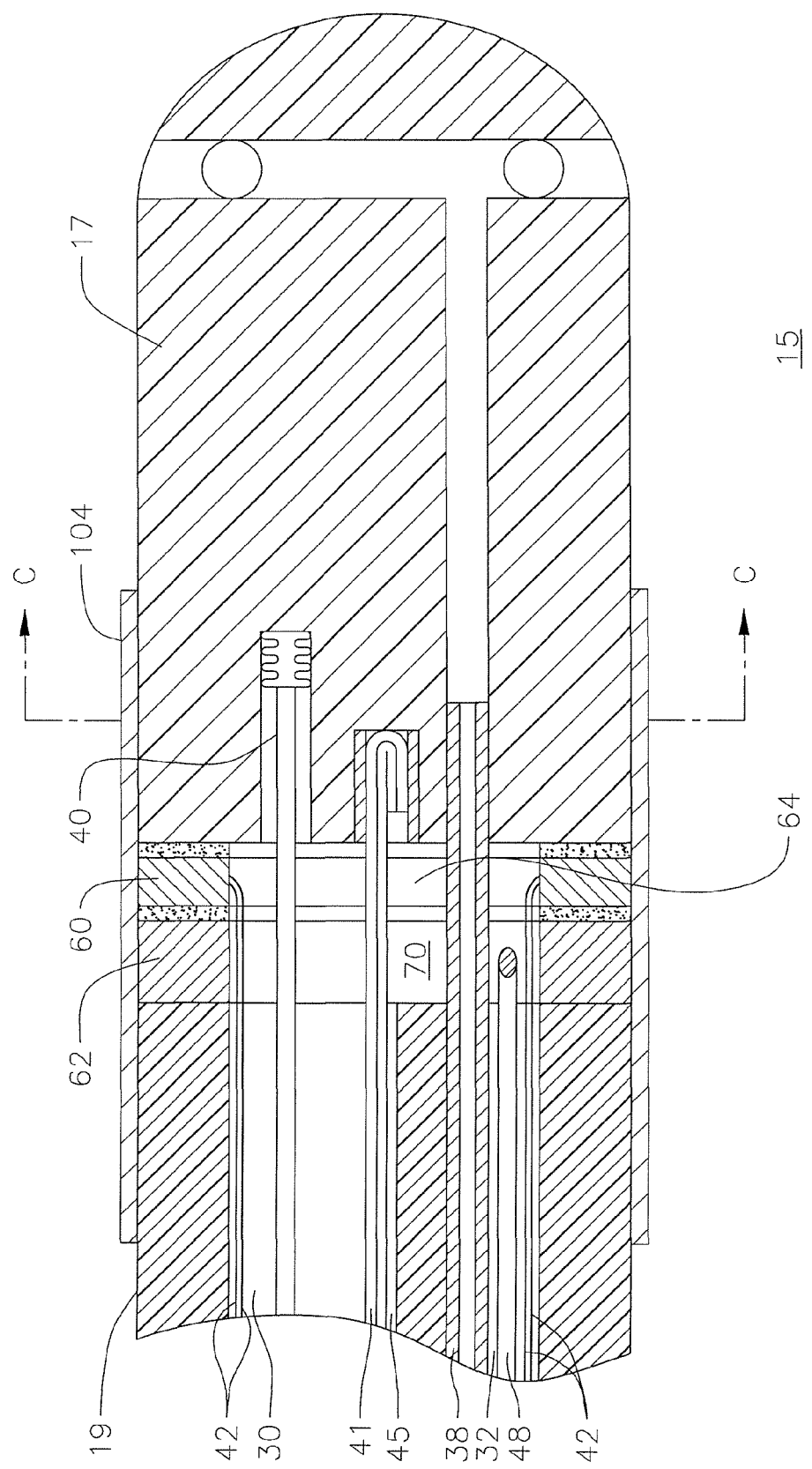
FIG. 4A is side cross-sectional view of the distal tip section of FIG. 3, as assembled, taken generally along a first diameter.

With reference to FIGS. 3, 4A and 4B, at the distal end of the intermediate section 14 is the tip section 15 that includes the tip electrode 17, the thin film pressure sensor 60 and a stop member 62 between the pressure sensor and the tubing 19. In the illustrated embodiment, the pressure sensor has a flattened annular or ring shape that is radially symmetrical. It has a thin planar construction and a circular cross-section having an outer diameter D1 and an inner diameter D2 defining a central lumen 64. The outer diameter D1 of the sensor is similar to or slightly less than an outer diameter of the tubing 19 and the tip electrode 17 such that a smooth and atraumatic profile is presented between the tubing 19 and the tip electrode 17 at or near the distal end of the catheter. The inner diameter D2 is sufficiently large to allow components, such as lead wires, irrigation tubing, thermocouple wires and/or sensor cable, to extend through it.

As shown in the embodiment of FIGS. 5 and 6, the thin-film pressure sensor 60 includes first trace electrodes 66 and second trace electrodes 68, each of which is formed on a respective thin, flexible supporting sheet 63 and 65, for example a polyester film such as MYLAR or KAPTON. The first electrodes 66 are formed on a distal surface of the first sheet 63 and the second electrodes are formed on a proximal surface of the second sheet 65. Each electrode has a thin coating 67 of a pressure-sensitive resistive material or ink such as molydenum disulphide that is spread over the support sheets. The sheets 63 and 65 overlie each other such that the first and second electrodes 66 and 68 face, overlie and cross each other, preferably at an angle, e.g., a right angle, to create a grid pattern of "intersections" X where each electrode of a pair is separated from the other electrode of the pair (and any other adjacent trace electrode(s)) by the pressure-sensitive resistive material (see FIG. 6A). An "intersecting" configuration as used herein describes a configuration where electrodes of an overlying pair cross each other but are not in contact with each other. Instead, the electrodes of a crossing pair at their closest proximity to each other remain separated by a gap or space 71 that is occupied by the pressure-sensitive material so that a change in the electrical resistivity in the pressure-sensitive material is detected by the crossing electrode pair. Thus, in the absence of an external force, the pressure-sensitive material 67 between the crossing electrodes provides a high resistance, and when an external force is applied and pressure on opposite sides of a crossing electrode pair changes, the resistance of the material changes in response thereto. With multiple pairs of crossing first and second electrodes, one electrode of each pair is driven and the other electrode of the pair is sensed such that measurement of the resistance between the driven and sensed electrodes for each crossing pair provides an output representative of the force applied to the pressure sensor. It is understood that triangulation processing can be applied by the microprocessor 13 to determine a force vector with directional (e.g., radial and axial) components.

The pressure sensor 60 has a thickness ranging between 0.05 mm and 0.5 mm and preferably is about 0.1 mm, and can be adapted and configured to take 1600 measurements per square inch ranging from 0.1 psi to 25 ksi (with forces as low as 62.5 μlb). Suitable thin-film pressure sensors and systems are available from Tekscan, Inc. of South Boston, Mass., USA and are described in U.S. Pat. Nos. 4,856,993 and 6,964,205, the entire contents of which are incorporated herein by reference. These sensors and systems can measure static and dynamic events and because they are extremely thin and flexible they can measure critical surface interface pressure with minimal interference and provide highly accurate pressure readings that can be processed by a processor and displayed on a monitor.

Each intersection or crossing pair is thus characterized by a variable resistance which is a function of the pressure applied thereto. It is understood that each electrode has an exposed terminal that is connected to a respective lead wire 42 that extends through the central lumen 64 of the pressure sensor and proximally through the catheter 10 to a suitable circuitry (not shown). The circuitry operates by sequentially scanning each crossing electrode pair of intersection to measure the resistance of the pressure-sensitive coating at that intersection to provide an indication of the force applied to the pressure sensor at that intersection.

In the illustrated embodiment of the catheter in FIGS. 5 and 6, the pressure sensor has a minimum of three electrode intersections with a load range and sensitivity appropriately selected for the expected range of contact forces. The minimum of three electrode intersections enables triangulation of the forces and/or pressures in determining force vectors with directional and angle information such as axial and/or radial components. As shown, each crossing is equally spaced from the outer and inner diameters and the crossings are equally spaced from each other around the longitudinal axis of the tip section, for example, at 0, 120 and 240 radial degrees. As understood by one of ordinary skill in the art, there can be any number of crossings as desired or appropriate depending on the resolution desired.

Figure 7:
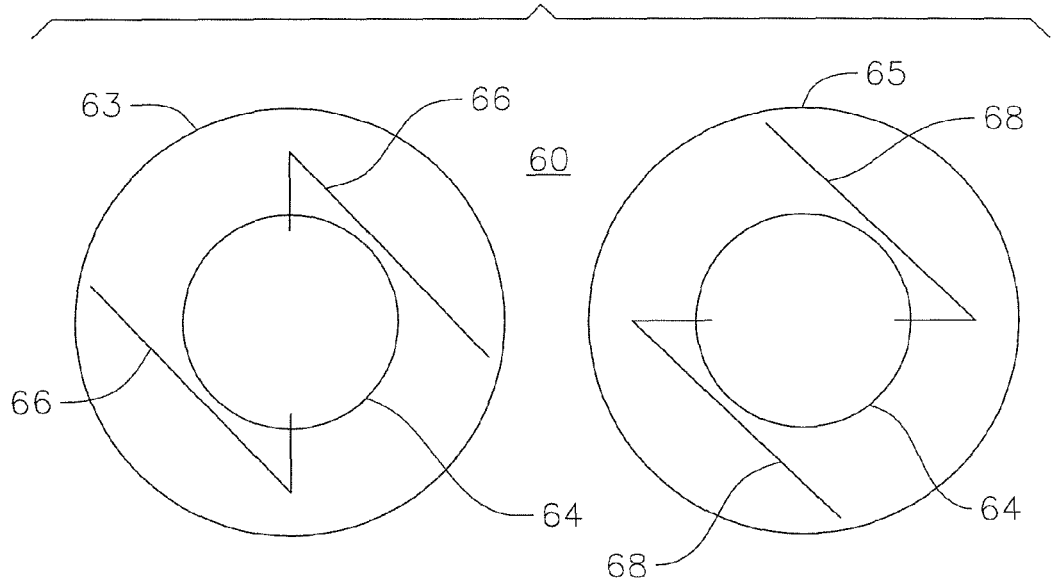
FIG. 7 is top plan view of an embodiment of a 2-D pressure sensor, with a first support member and a second support member before assembly.
Figure 8:
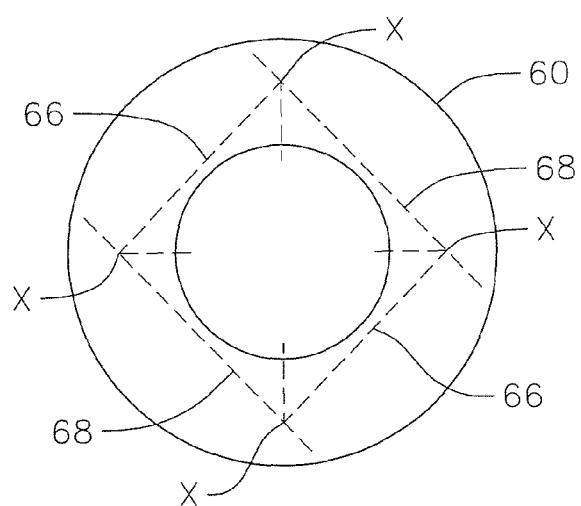
FIG. 8 is a top plan view of the 2-D pressure sensor of FIG. 7, as assembled.

In the alternate embodiment of FIGS. 7 and 8, the sensor includes at least two parallel driven electrodes 66 and two parallel sensed electrodes 68 that are arranged to provide four crossings X that are equi-distanced from each other so that the four crossings form four corners of a square configuration where the crossings are radially symmetrical around the longitudinal axis of the tip section. It is understood that any number of electrodes can be arranged in any suitable pattern and that electrodes can be consistently driven or consistently sensed, or that with an appropriate circuitry the same electrode(s) can alternate between being driven and being sensed, as needed. Indeed, as understood by one of ordinary skill in the art, the present system with the appropriate circuitry can employ any suitable number of electrodes arranged as driven and/or sensed electrodes.

In the illustrated embodiment of FIGS. 3, 4A and 4B, the stop member 62 is proximal of the pressure sensor 60 and acts as a rigid foundation for the pressure sensor. The member is disc shaped having a thicker planar construction and a circular cross-section having an outer diameter D3 and an inner diameter D4 defining a central lumen 70. The outer diameter is similar to or slightly less than an outer diameter of the tubing 19 and the tip electrode 17 such that a smooth and atraumatic profile is presented between the tubing 19 and the tip electrode 17 at or near the distal end of the catheter. The inner diameter is sufficiently large to allow the aforementioned components to extend between the tubing 19 and the tip electrode 17. The thickness of the stop member between a distal planar surface and a proximal planar surface ranges between about 0.4 mm and 0.5 mm. The material of the member can be any material that is sufficiently rigid under forces ranging between about 5 and 150 gf.

Distal surface of the stop member and/or proximal surface of the tip electrode are generally planar and perpendicular to the longitudinal axis of the distal tip section so that the pressure sensor sandwiched therebetween detects primarily axial forces acting on the tip electrode, although measurement of radial components is also possible through analysis of differences in the measured axial components of the force acting on the tip electrode. These surfaces can include raised formations equally spaced about the longitudinal axis which act to localize forces to the grid intersections of the pressure sensor. In the illustrated embodiment, the proximal surface of the tip electrode has a plurality of circular mounds 74 which plurality is equal to the plurality of electrode intersections X in the pressure sensor. As illustrated, each mound is situated in axial alignment with a respective electrode intersections for localizing forces applied to the tip electrode to the intersections X of the pressure sensor.

It is understood that the while the words "pressure" and "force" have different technical meaning and units of measurement, these terms are used interchangeably herein as the pressure sensor is configured with the electrode intersections at various intervals (with pre-determined area of coverage for each intersection) allowing for the signals to be displayed as pressure. Thus, the representation of any particular area depends on the plurality of intersections in that area, with a greater plurality providing a greater representation and a lesser plurality providing a lesser representation. In that regard, where the raised formations of the stop member and/ or the proximal end of the tip electrode have known surface areas, results of measurements taken can be determined in terms of force values. As such, multiple electrode junctions are advantageously utilized to determine force components and by triangulation, force vectors.

Figure 4C:
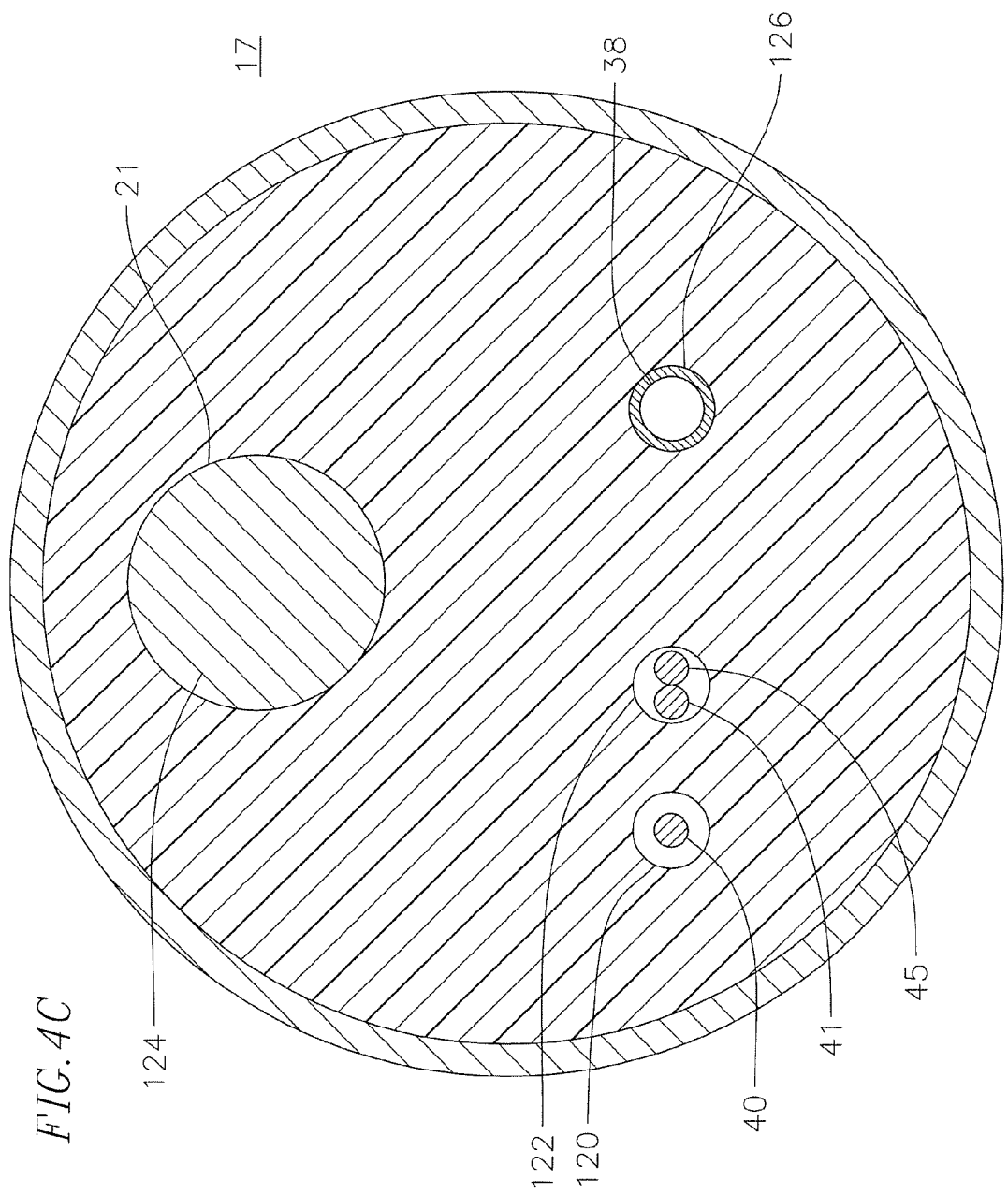
FIG. 4c is an end cross-sectional view of the distal tip section of FIGS. 4A and 4B, taken along line C-C.

As best seen in FIG. 4C, distal ends of the tip electrode lead wire 40 and the thermocouple wires 41 and 45 are anchored in blind holes 120 and 122, respectively, formed in the proximal end of the tip electrode 17. The electromagnetic position sensor 21 is received in the blind hole 124. The irrigation tubing 38 extends into irrigation passage 126 formed at the proximal end of the tip electrode. The passage 126 is in communication with radial transverse branches 130 to allow fluid delivered by the irrigation tubing 38 to exit to outside of the tip electrode via a plurality of radial ports 132.

Figure 9:
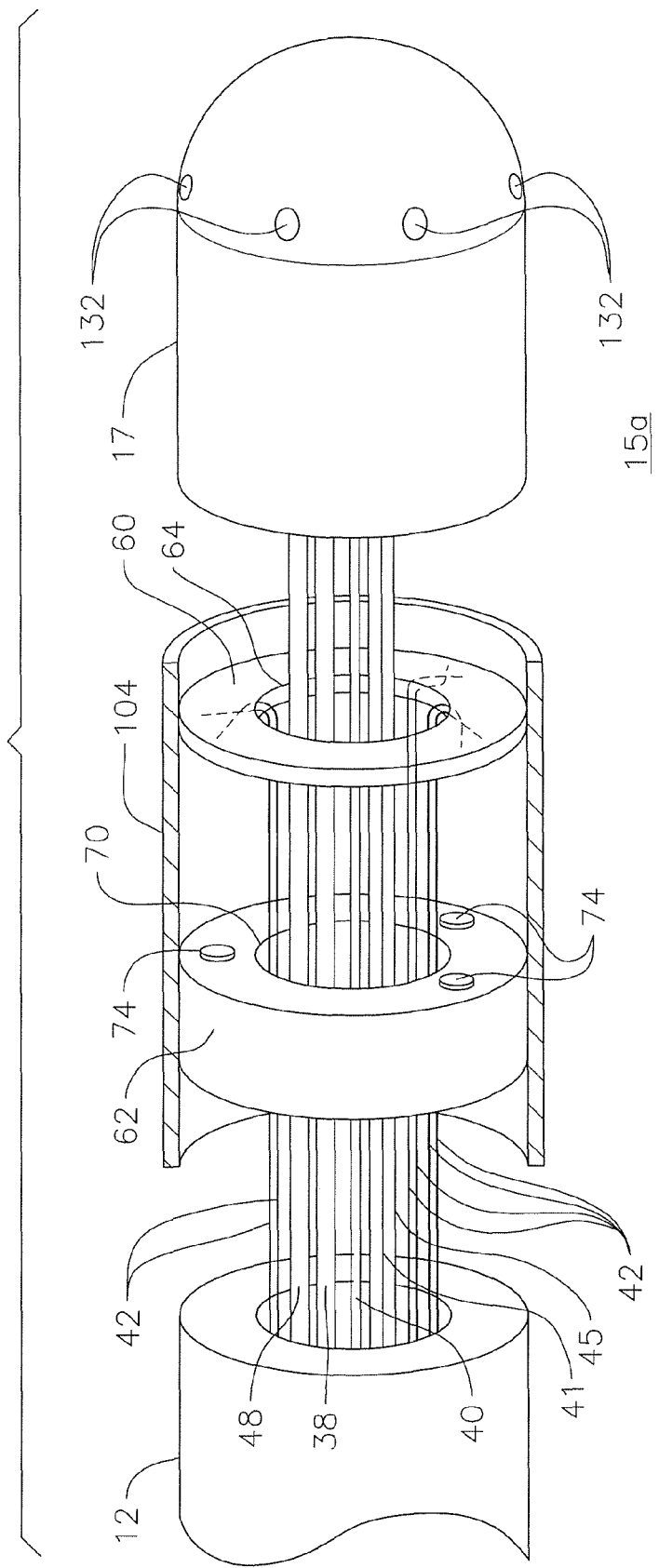
FIG. 9 is an alternate embodiment of a catheter with a 2-D pressure sensor, with a catheter body joined to a distal tip section.
Figure 9A:
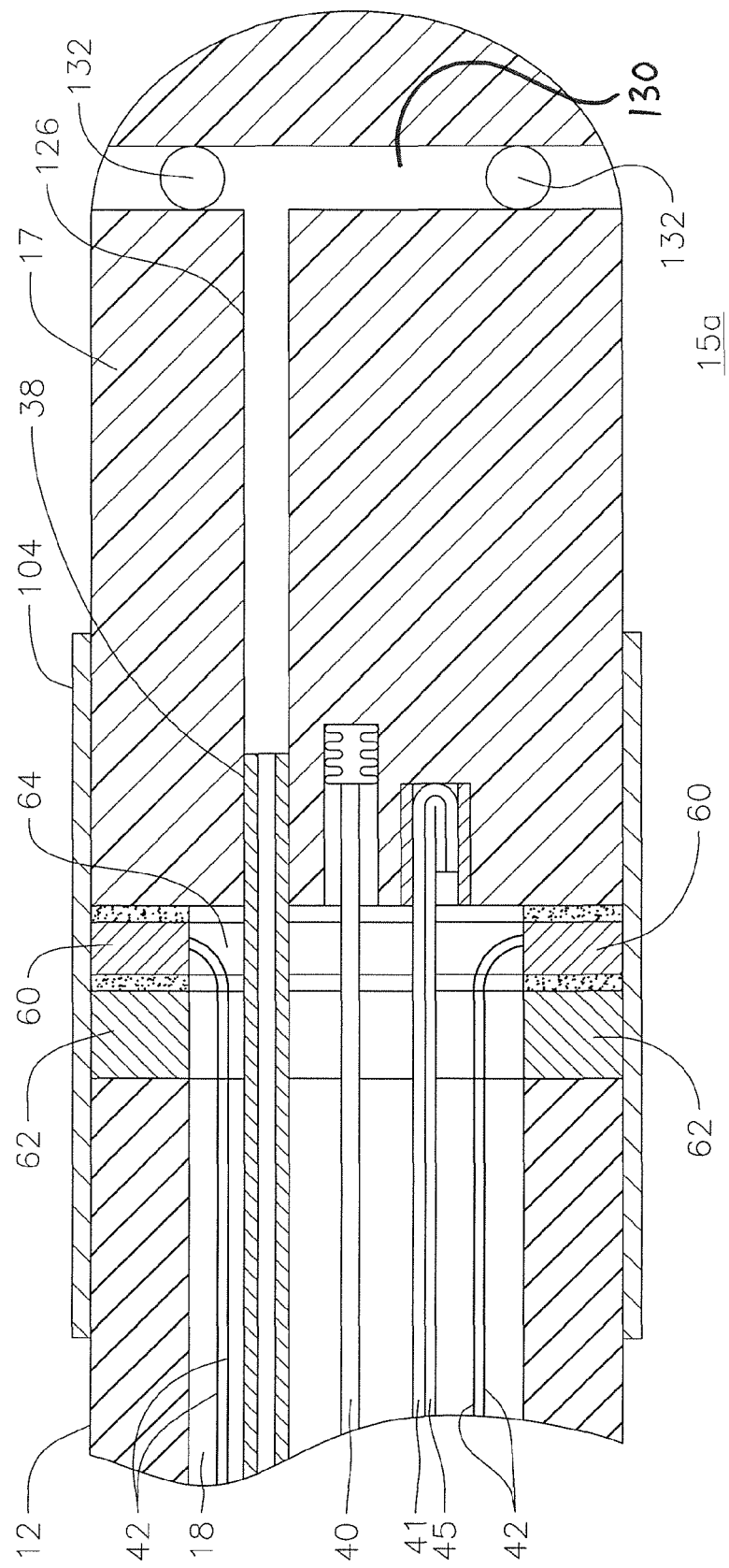
FIG. 9A is a side cross-sectional view of the catheter of FIG. 9.

As described, the catheter 10 is suited for bi-directional deflection with user control of the puller wires via the deflection member on the control handle. However, an embodiment of a catheter 10a adapted for use with a guiding sheath is illustrated in FIG. 9. The catheter 10' is without a multi-lumen tubing deflectable by puller wires. As shown, the distal end of the catheter body 12 is attached to the distal tip section 15, without an intermediate portion in between, with the components passing between the central lumen 18 of the catheter body 12 and the central lumens of the stop member 62 and the pressure sensor 60.

Figure 10:
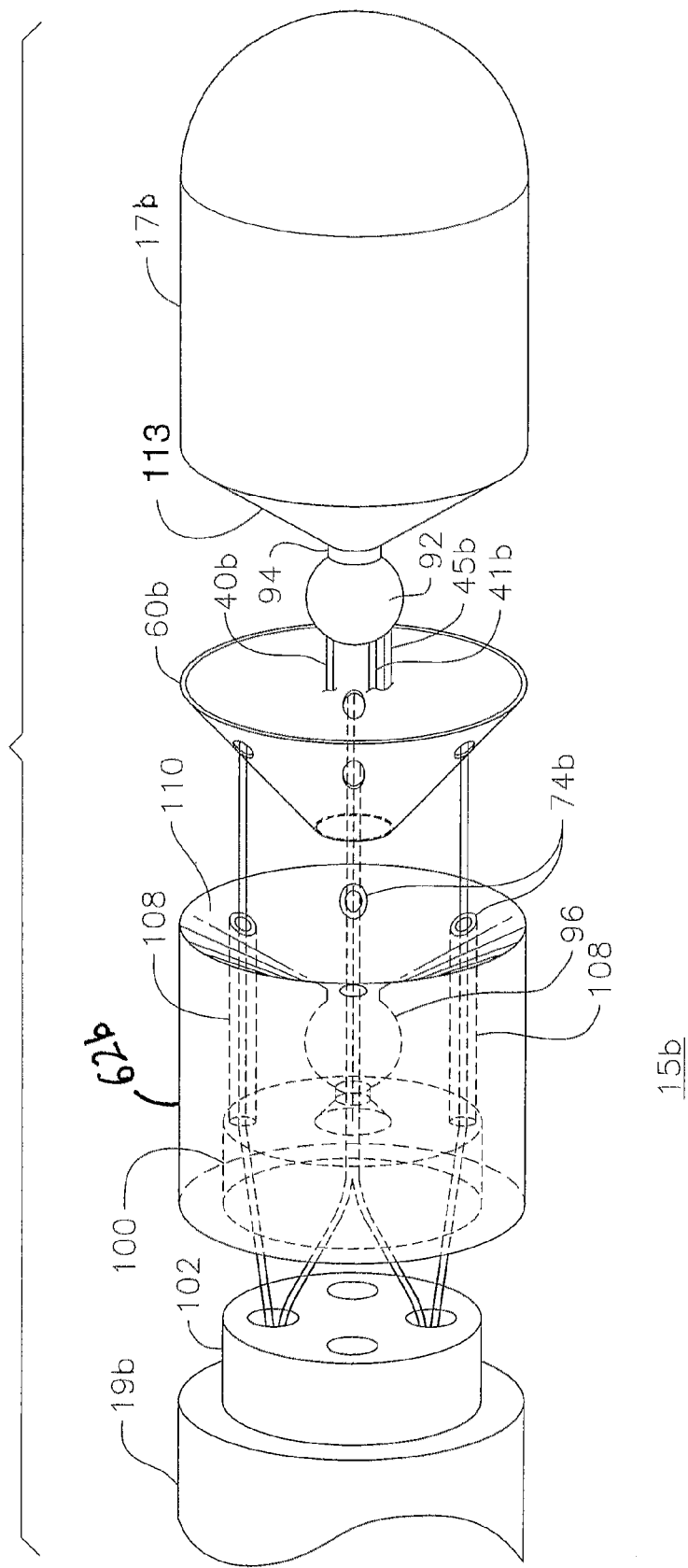
FIG. 10 is an exploded view of an embodiment of a distal tip section of the catheter of the present invention, including a 3-D pressure sensor.
Figure 11:
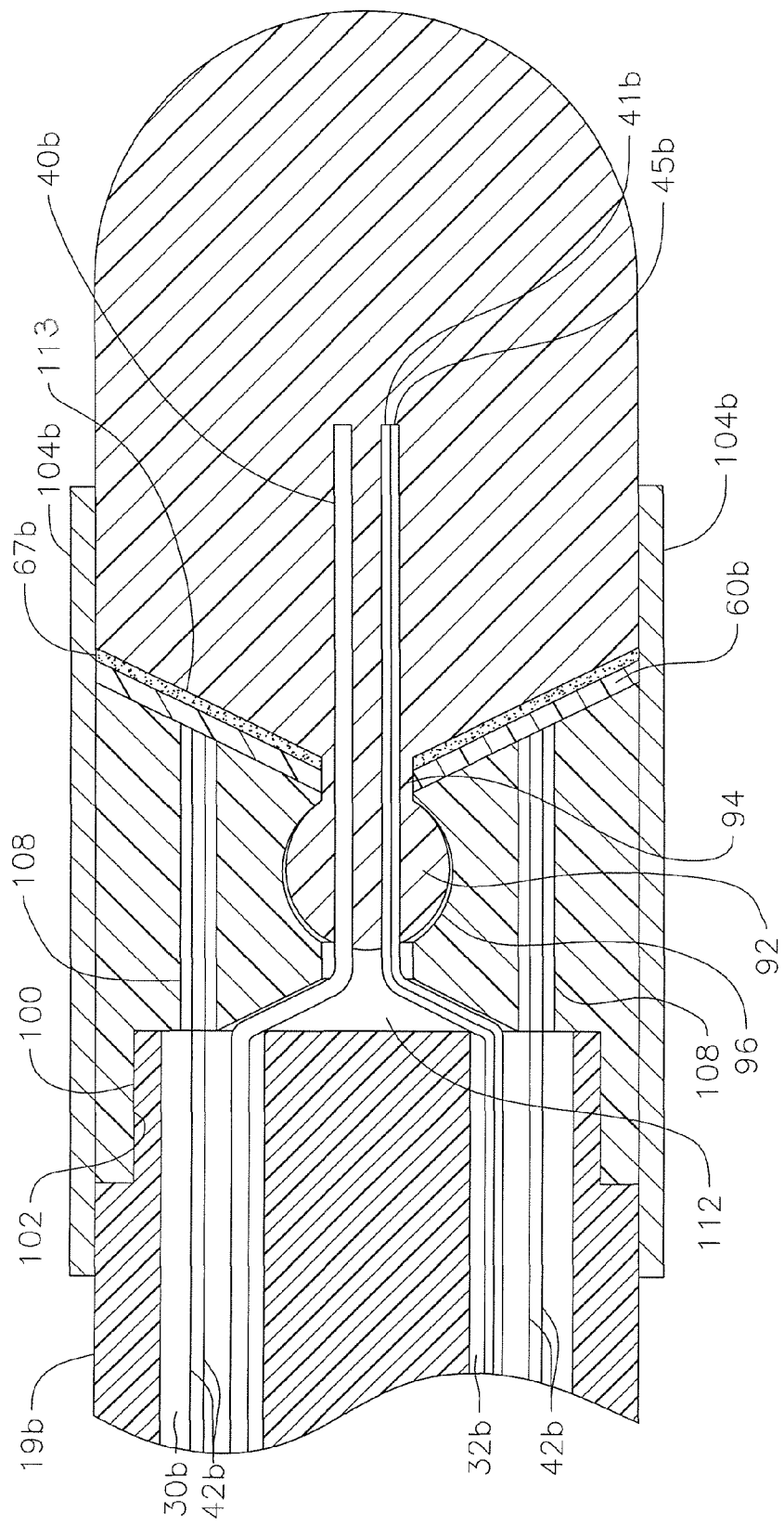
FIG. 11 is side cross-sectional view of the distal tip section of FIG. 10, as assembled.
Figure 12:
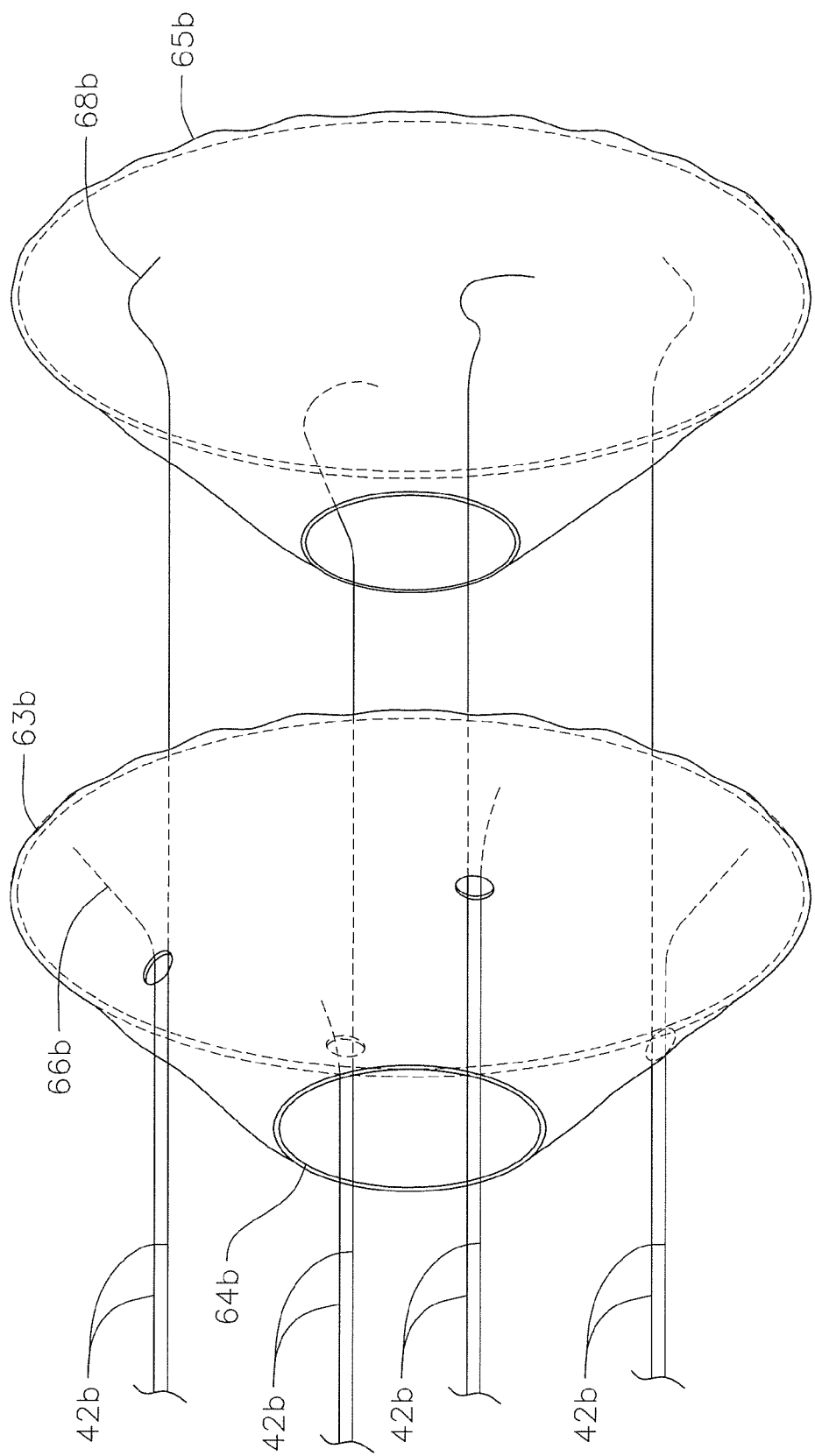
FIG. 12 is an exploded view of the 3-D pressure sensor, without the pressure-sensitive material.

In another alternate embodiment of a catheter 10b illustrated in FIGS. 10, 11 and 12, in which similar components have similar reference numerals, a distal tip section 15b includes a thin film pressure sensor 60b that has a 3-D shape, e.g., a conical shape, such that each location on the proximal and distal surfaces has a surface vector with an axial and radial component. In this embodiment, the pressure sensor includes four electrode intersections X, each equally spaced from the outer diameter and the inner diameter of the conical shape, and equally spaced from each other around conical shape, for example, at 0, 90, 180 and 270 degrees around the longitudinal axis of the distal tip section. Second electrodes 68b are supported on a proximal surface of a first or distal thin, flexible supporting sheet 65b that has a conical shape. First electrodes 66b are supported on a distal surface of a second or proximal thin, flexible supporting sheet 63b that also has a conical shape and is slightly larger than the first supporting sheet so that the second sheet can accommodate and surround both the first sheet and the pressure-sensitive material 67b applied to the distal surface of the first sheet and the proximal surface of the second sheet to form the pressure sensor. As illustrated, first and second electrodes are arranged on their respective sheet to form intersections X at radially-symmetrical locations around central lumen 64b. Corresponding holes 90 are provided in the proximal supporting sheet 63b so that lead wires 42b for both the first and second electrodes can extend proximally toward stop member 62b.

The conical shape of the pressure sensor 60b generally matches and corresponds with a concave conical distal surface 110 of stop member 62b and a convex conical proximal surface 113 of tip electrode 17b such that the pressure sensor is nested between the tip electrode and the stop member with raised formations, e.g., raised ring-shape mounds 74b, axially aligned with the electrode intersections. The central lumen 64b allows components to extend through the pressure sensor 60b, which in the instant embodiment, includes a protrusion having a ball member 92 and a neck 94 that are aligned with the longitudinal axis of the tip electrode and extend proximally from a main body of the tip electrode 17b. The ball member is received in and interlocks with a socket formed 96 in the distal end of stop member. The ball and socket coupling provides additional axial tensile strength by providing a mechanical interference between the tip electrode and the stop member. In that regard, any staking interference such as with a flattened end or post can be used. Moreover, the ball socket coupling allows for movement of the tip electrode 17b in more dimensions relative to the stop member 62b for increased sensitivity and higher resolution in detecting applied forces with radial and axial components. The thickness of the stop member 62b between its distal and proximal surfaces ranges between about 1.0 mm and 6.0 mm, and preferably about 3.0 mm. The proximal surface of the stop member is notched with an inner circumference 100 to receive an outer circumference 102 of a notched distal end of tubing 19b of the intermediate section 14. Lead wires 42b for the pressure sensor electrodes 66b and 68b extend through axial passages 108 provided in the stop member 62b that are axially aligned with the electrode intersections X. Tip electrode lead wire 40b and thermocouple wires 41b and 45b pass through a central passage 112 that connects inner notched proximal end 100 of the stop member with the concave distal surface of the stop member. Tip electrode lead wire 40 and thermocouple wires 41, 45 are anchored in their respective blind holes formed in the convex proximal end of the tip electrode.

In any of the foregoing embodiments, the pressure sensor can be bonded to the tip electrode and/or the stop member with any adhesive adapted to withstanding axial loads of a minimum of about 15 Newtons, such as when the tip electrode comes in contact with tissue during mapping and ablation. Suitable adhesives, including epoxy, polyurethane and the like, should be rigid enough to transfer force to the pressure sensor without loss but should be sufficiently elastic so as not to cause plastic deformation in the intended range of forces to act on the catheter.

A flexible protective cover, for example, a thin flexible, single-lumen extrusion or tubing 104, can be mounted over the pressure sensor and the stop member to insulate these components and their interior from patient contact.

For a catheter with N number grid intersections, the sum of the axial components of each measured force $F_{1,axial}$ through $F_{N,axial}$ should be equal to the axial component of the force applied to the tip electrode. For conical shaped sensors, the sum of the radial components of each measured force $F_{1,radial}$ through $F_{N,radial}$ should be equal to the radial component of the force applied to the tip electrode. In the case of a purely axial applied load, the axial component of each measured force would be equivalent to (1/N) time the magnitude of the applied force and the sum of the radial components of measured forces would equal zero. As the applied force changes from purely axial, changes in the components of each measure force allows for determination of the magnitude and direction of the applied force.

The illustrated embodiment of the catheter 10b is adapted for bi-directional deflection by means of a pair of puller wires that extend through two opposite lumens of the tubing 19b of the intermediate section 14b. However, it is understood that the catheter 10b can also be adapted for use with a guiding sheath where a catheter body is joined to the distal tip section without an intermediate section.

As far as pressure vs force goes, I believe both terminologies are correct. These sensors typically place the junctions at various intervals (pre-determined area of coverage for each junction) allowing for the recorded signal to be displayed as pressure. In the disclosed concept, the number of junction is more limited and therefore each is less representative of the area that they cover. However, as mentioned in paragraph 0047, the stop member and proximal end of the tip electrode may have raised surfaces (ideally of know surface areas). These surface will allow the measurements to be taken for known areas allowing the results to be determined in terms of force values. Because of this, multiple pressure sensors are being utilized to determine force components and by triangulation, force vectors.

The preceding description has been presented with reference to certain exemplary embodiments of the invention. The drawings shown wherein are not necessarily to scale. Workers skilled in the art and technology to which this invention pertains will appreciate that alterations and changes to the described structure may be practiced without meaningfully departing from the principal, spirit and scope of this invention. It is understood that the drawings are not necessarily to scale. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A catheter adapted for mapping and/or ablation, comprising:
    a tubing adapted for passage through a vessel in a patient's body;
    a tip electrode distal the tubing, the tip electrode configured for contact with body tissue for mapping or ablation; and
    a thin, flexible force sensor distal the tubing, the force sensor having:
    first and second thin flexible backing sheets;
    a first flexible electrode and a second flexible electrode, the first flexible electrode attached to and supported by the first thin flexible backing sheet to provide a driven electrode, the second flexible electrode attached to and supported by the second thin flexible backing sheet to provide a sensed electrode; and
    a resistive layer applied to at least one of the sensed or driven electrodes and made of a resistive material whose resistance changes as a function of the pressure applied thereto.

2. A catheter of claim 1, wherein the first flexible electrode and the second flexible electrode comprise at least two pairs of first flexible electrodes and second flexible electrodes, wherein the first flexible electrodes are attached to and supported by the first thin flexible backing sheet to provide at least two driven electrodes, and the second flexible electrodes are attached to and supported by the second thin flexible backing sheet to provide at least two sensed electrodes, and wherein the resistive layer is applied to at least one of the sensed electrodes or the driven electrodes.

3. A catheter of claim 2, wherein the at least two pairs of first flexible electrodes and second flexible electrodes form at least four crossings, each crossing being between one of the first flexible electrodes and one of the second flexible electrodes.

4. A catheter of claim 1, further comprising a stop member positioned between the tubing and the force sensor, the stop member being more rigid than the tubing for providing a normal force against the force sensor in response to a force applied to the tip electrode.

5. A catheter of claim 1, further comprising a stop member positioned between the tubing and the force sensor, wherein a distal end of the stop member and a proximal end of the tip electrode have a conforming configuration such that the force sensor is nested therebetween.

6. A catheter of claim 5, wherein the conforming configuration includes a generally conical shape.

7. A catheter of claim 6, wherein each of the distal end of the stop member, the proximal end of the tip electrode, and the force sensor has a generally conical shape.

8. A catheter of claim 7, wherein the distal end of the stop member has a generally concave conical shape and the proximal end of the tip electrode has a generally convex conical shape.

9. A catheter of claim 1, wherein the force sensor is disc-shaped and positioned between the tubing and the tip electrode.

10. A catheter of claim 9, wherein the force sensor has an outer diameter and an inner diameter defining a hole.

11. A catheter of claim 1, wherein the tubing has a single central lumen.

12. A catheter of claim 1, wherein the tubing supports a catheter body.

13. A catheter of claim 1, wherein the tubing is multi-lumen.

14. A catheter of claim 1, wherein the tubing supports a deflectable portion.

15. A catheter adapted for mapping and/or ablation, comprising:
   a tubing adapted for passage through a vessel in a patient's body;
   a tip electrode distal the tubing, the tip electrode configured for contact with body tissue for mapping or ablation; and
   a thin, flexible force sensor distal the tubing, the force sensor having
      first and second thin flexible backing sheets;
      a plurality of electrodes between the first and second backing sheets, the electrodes arranged to form a plurality of crossings with different pairs of the plurality of electrodes, each electrode being attached to and supported by at least one of the first or second flexible backing sheets, wherein for each pair of electrodes for each crossing one electrode is driven while the other electrode is sensed; and
      a resistive layer applied to at least one of the sensed or driven electrodes and made of a resistive material whose resistance changes as a function of the pressure applied thereto.

16. A catheter of claim 15, further comprising a stop member, wherein the force sensor is positioned between the stop member and the tip electrode.

17. A catheter of claim 16, wherein an adjacent end of the stop member and an adjacent end of the tip electrode have a conforming 3-D shape such that the force sensor is nested therebetween.

18. A catheter of claim 15, wherein the force sensor has a three-dimensional shape such that it is responsive to a force vector applied to the tip electrode with axial and radial components.

19. A catheter of claim 15, wherein the force sensor is responsive to a force vector applied to the tip electrode with axial and radial components.

20. A catheter of claim 15, wherein the force sensor has at least three crossings.

\* \* \* \* \*

UNITED STATES PATENT AND TRADEMARK OFFICE
CERTIFICATE OF CORRECTION

PATENT NO. : 8,380,276 B2
APPLICATION NO. : 12/857342
DATED : February 19, 2013
INVENTOR(S) : Jeffrey W. Schultz It is certified that error appears in the above-identified patent and that said Letters Patent is hereby corrected as shown below:

On the Title Page

(56) References Cited, page 2, U.S.     Delete "Leatham et al."
PATENT DOCUMENTS, line 40     Insert -- Schwartz et al. --

Signed and Sealed this
Eighteenth Day of February, 2014

Michelle K. Lee
*Deputy Director of the United States Patent and Trademark Office*